United States Patent
Shettigar

[19]

[11] Patent Number: 5,215,519
[45] Date of Patent: Jun. 1, 1993

[54] AUTOTRANSFUSION MEMBRANE SYSTEM WITH MEANS FOR PROVIDING REVERSE FILTRATION

[76] Inventor: U. Ramakrishna Shettigar, 4555 Peach St., Salt Lake City, Utah 84113

[21] Appl. No.: 730,705

[22] Filed: Jul. 16, 1991

Related U.S. Application Data

[63] Continuation-in-part of Ser. No. 525,536, May 18, 1990, Pat. No. 5,055,198, which is a continuation-in-part of Ser. No. 491,183, Mar. 7, 1990, abandoned.

[51] Int. Cl.$^5$ ................. A61M 37/00; A61M 1/14
[52] U.S. Cl. ................................... 604/4; 604/6; 422/44
[58] Field of Search ........................... 604/4-6, 604/27-28, 236, 267, 317, 319; 422/44-48

[56] References Cited

U.S. PATENT DOCUMENTS

| | | |
|---|---|---|
| 2,804,075 | 8/1957 | Borden . |
| 3,965,896 | 6/1976 | Swank . |
| 3,993,067 | 11/1976 | Schachet et al. . |
| 4,014,329 | 3/1977 | Welch et al. . |
| 4,033,345 | 7/1977 | Sorenson et al. . |
| 4,631,050 | 12/1986 | Reed et al. . |
| 4,772,256 | 9/1988 | Lane et al. . |
| 4,796,644 | 1/1989 | Polaschegg . |
| 4,798,578 | 1/1989 | Ranford . |
| 4,874,359 | 10/1989 | White et al. . |
| 4,886,487 | 12/1989 | Solem et al. . |
| 4,898,572 | 2/1990 | Surugue nee Lasnier et al. . |
| 4,976,682 | 12/1990 | Lane et al. . |

*Primary Examiner*—Randall L. Green
*Assistant Examiner*—R. Clarke
*Attorney, Agent, or Firm*—Trask, Britt & Rossa

[57] ABSTRACT

An apparatus for recycling autologous blood from a patient for reinfusion back to the patient comprising suction means, means for admixing aspirated blood with a washing fluid, filtering means for filtering the admixture through an emboli filter, monitoring means for measuring the blood component levels or hematocrit in the filtered blood, filtration means for removing excess fluid and particulates from the blood, and reinfusion means is disclosed. The apparatus operates in three different modes—idling, filtration and reinfusion—in response to specified conditions. Embodiments for use during surgery for on-line purification and reinfusion on a real time basis are disclosed along with embodiments for use postsurgically when the wound site is closed. Means for performing reverse filtration in the membrane filter are also included for maintaining a consistent level of filtration through the membrane filter.

25 Claims, 13 Drawing Sheets

AUTOTRANSFUSION MEMBRANE SYSTEM WITH MEANS FOR PROVIDING REVERSE FILTRATION

BACKGROUND OF THE INVENTION

1. Related Applications

This application is a continuation-in-part of applicant's co-pending application Ser. No. 525,536 filed May 18, 1990, now U.S. Pat. No. 5,055,198 the contents of which are incorporated herein by this reference, which is a continuation-in-part of Ser. No. 491,183 filed Mar. 7, 1990, now abandoned.

1. Field of the Invention

This invention relates generally to methods and apparatus for treating blood lost at a wound site, during a surgical procedure or during a postsurgical management period. More specifically, the present invention relates to recovery, purification and reinfusion of blood aspirated from a wound site during intraoperative or postsurgical recovery periods, on-line purification of aspirated blood by filtration and cell-washing using membranes, and reinfusion of purified autologous blood to the patient on a real time basis.

3. State of the Art

Significant blood loss to a person may occur during a traumatic injury, such as an auto accident, or during serious and prolonged surgery, such as open heart surgery. Significant amounts of blood may even be lost during postsurgical recovery periods due to hemorrhagic conditions. Significant loss of blood results in decreased blood pressure, decreased cardiac output and decreased oxygen delivery to tissues, particularly brain cells. For these reasons, it is necessary to compensate the loss of blood by transfusing blood into the patient as soon as possible.

During an intraoperative period, a pool of shed blood accumulates in the wound site, which obstructs the surgery unless it is aspirated out of the wound site. Usually, suction is provided to remove the shed blood, other accumulated fluids, blood clots and other tissue debris. Total loss of blood may range from about 1,000 ml to about 15,000 ml depending on the extent and traumatic conditions of the surgery.

During a postsurgical recovery period, the closed wound may continue to bleed into the chest, pleural, or abdominal cavity due to hemorrhagic conditions. On average, 1,000 milliliters (ml) of blood is usually lost over a five hour period of postsurgical recovery. Blood loss could be as high as 21,350 ml. In such instances, the patient may have to be rushed back to surgery to correct the underlying problem. Blood transfusion is imperative under such conditions.

By conventional methods, shed blood is drained from the body cavity using drainage tubing under controlled suction. The drained blood is generally collected into a container. Blood shed during intraoperative or postsurgical recovery periods can be collected in a container and reinfused to the patient provided the salvaged blood is free of impurities. Typical impurities are blood clots, tissue debris, hair, foreign particles, activated coagulation factors, denatured proteins, plasma free hemoglobin, and any other fluids (e.g. irrigation fluid) that are being introduced into the wound site by medical personnel.

Because of these impurities, salvaged blood is usually filtered using a micron filter to remove particles greater than a particular size, for example, forty microns. The blood is then subjected to "cell-wash." Cell washing technique may involve mixing blood with a physiological solution (e.g., saline or Ringer's solution) and then centrifuging the diluted blood in order to recover the heavier blood cells which are suitable for reinfusion to the patient. However, the lighter portion of centrifuged fluid (i.e., the top portion of the centrifuge tube content) containing platelets, white cells, plasma proteins and antibodies is usually discarded as waste. This is a significant loss to the patient, particularly the loss of coagulation factors, platelets, white cells and antibodies. Therefore, the efficiency of recovery of blood products by conventional cell washing techniques is low. Additionally, conventional blood recovery methods are not on-line, real time processes, but batch processes involving operator intervention and are subject to human errors and time delay.

Thus it will be appreciated that known apparatus for purification of salvaged blood based on cell-centrifuge machines are not designed to work on a real time basis. That is, there is considerable lag time (more than 15 minutes) between the moment of aspiration of blood and reinfusion of processed autologous blood. The time differential is a significant problem, especially when the patient bleeds rapidly and his/her lost blood volume should be compensated immediately. Furthermore, during cell washing by the centrifuge technique, a significant amount of red blood cells are lost as well as almost all white blood cells, platelets and plasma proteins, including antibodies.

Due to the aforementioned problems in the conventional cell washing technique, a patient is usually given homologous (donor) blood transfusions rather than his/her own blood which is still being processed. Problems with homologous blood transfusion are many. The major problem is providing suitable donor blood which will not cause side effects such as anaphylactic reactions, and which does not contain donor-associated infections such as hepatitis, malaria or acquired immune deficiency syndrome (AIDS). At times, it is difficult to find appropriate types and amounts of blood necessary for transfusions and it can become very expensive.

In view of the aforementioned problems, "autotransfusion" (reuse of a patient's own blood) has received significant attention. A number of autotransfusion systems have been developed in recent years with varying system conformations. They may be composed of any of three basic units; an aspirator unit, a cell washing unit, and a reinfusion unit.

The typical aspirator unit consists of a suction handle attached to suction tubing, which in turn is connected to an emboli filter. The emboli filter may be provided with some means of applying positive or negative pressure. It may also include a degassifier, a micron filter, and a blood reservoir. Controlled suction may be applied with a vacuum source via a vent line. Some blood recovery systems, by contrast, provide positive pressure to facilitate filtration. Shed blood and other impurities are thereby aspirated from the wound site and delivered to the emboli filter. Large impurities are trapped in the micron filter.

Blood from the filter is usually pumped to a cell centrifuge machine, where it is mixed with an appropriate "washing fluid" and centrifuged for a specified time period until the heavier blood cells are separated from the plasma. This method is too cumbersome, time consuming, and requires an operator to attend to the system continuously. Furthermore, there is a loss of precious plasma proteins, antibodies, and white blood cells which are important in order for the body to fight infection. Indeed, blood components may be damaged or destroyed by such apparatus. Additionally, many porous membrane filtration systems typically become clogged due to debris and blood components becoming lodged in the pores of the membrane. Under such conditions, the filter must be removed and replaced which is time consuming and expensive.

Thus, it would be an advancement in the art to provide on-line continuous methods and apparatus which would minimize loss of precious blood elements and which would reinfuse to the patient his/her own blood on a real time basis. It would be a further advancement to provide an automatic system which would reinfuse whole blood at a specified hematocrit level free of air emboli. It would be a further advancement to provide means for removing debris from clogged filters to maintain consistent filtration throughout the surgical or post-surgical procedure.

The aforementioned systems are generally designed for use during surgery (i.e., intraoperative period) when bleeding rates may be as high as three liters per minute, and when the shed blood aspirated from the open wound site may contain some air. For these reasons, intraoperative autotransfusion systems usually are designed to remove air emboli and to process large amounts of blood.

During the post-surgical recovery period, bleeding may continue at the site of the closed wound, but at a significantly reduced flow rate; usually at about 1,000 ml over a five hour period. Blood losses can range, however, from about 2,050 ml to about 21,350 ml. Since the wound-site is closed, the blood is generally not in contact with air. The shed blood is usually drained using a drainage unit having controlled suction. Examples of such drainage units are the "Pleur-evac" chest drainage unit by Deknatel, Howmedica, Inc., New York; "Sentinel Seal Compact "chest drainage unit" by Argyle; "Snyder Hemovac Compact Evacuator", Zimmer Corp., Dover, Ohio; and "Sorenson Autotransfusion system", Salt Lake City, Utah. In all these drainage units, a controlled suction (i.e., where negative pressure does not exceed −25 cm of water) is applied to drain the shed blood from the closed wound site via one or two drainage tubes. The drained blood is filtered to remove solid particulates, and is collected in a bag. When a suitable volume of blood is collected, it is reinfused to the patient directly without washing the blood cells. The reclaimed blood may be washed with saline solution using a cell centrifuge machine, however.

None of the aforementioned systems wash the blood on-line. Rather, cell washing heretofore has been done in a batch operation using a cell centrifuge. Since controlled suction is applied to the drainage tubing using a vacuum pump, the blood-air interface is not completely eliminated in such systems. Thus, it would be an advancement in the art to provide an automatic post-surgical autotransfusion system which eliminates the problems described above.

SUMMARY OF THE INVENTION

The invention is generally directed to the filtration and processing of blood aspirated from a patient, either during or after surgery, for ultimate reinfusion into the patient. The invention includes means for aspirating blood from the wound site, means for admixing a washing fluid with the aspirated blood, means for filtering from the blood air emboli, particulate matter, unwanted blood or other cellular components, and excess fluid, and means for reinfusing of the purified blood into the patient. The invention may also include means for maintaining consistent filtration and treatment of aspirated blood by unclogging accumulated debris from the filtration membranes.

The invention may be directed to use during a surgical procedure when the wound site is open, and may also be directed to use during postsurgical recovery for draining blood which may be lost from a closed wound site as a result of hemorrhagic conditions.

The aspiration means for aspirating blood from a wound site may typically include a suction tip and handle for directing the suction tip into the wound site. Aspiration is accomplished by attachment of a vacuum source to the system which applies negative pressure of up to −200 mm Hg. Washing fluid, which aids in removal of impurities, is retained in a suitable retainer means and is mixed with the aspirated blood. The washing fluid may be any type including conventional fluids used in surgery, such as normal saline or Ringer's solution. The washing fluid may contain an anticoagulant substance, such as heparin. To optimize the removal of impurities, the washing solution is admixed in proportion to the amount of blood aspirated. The proportion or ratio of washing solution to blood may vary from between about one to one to about one to three.

Assurance of optimal ratios of blood and washing fluid may be accomplished by maintaining the washing fluid retainer at a level lower than the suction means so that when no blood is being aspirated, the negative pressure created by the vacuum in the suction means is too low to draw any washing fluid into the system. Conversely, when blood is being aspirated into the system, the resulting increase in negative pressure urges washing fluid from the retainer means into the system. Therefore, washing fluid may be introduced into the system at a rate proportional to the rate of bleeding by using a tube for aspirating blood which is equal in size to a tube for feeding washing fluid into the system. Similarly, proportions of blood to washing fluid can be selected by varying the relative sizes of the tubes, or by varying the relative heights of the washing fluid bag.

The present invention provides a continuous on-line method of removing air, impurities, unwanted cellular and blood components, and excess fluid. The blood and washing fluid admixture is directed through an emboli filter which traps and removes air bubbles from the admixture. The emboli filter is also capable of trapping particulate matter of relatively large size. The blood and washing fluid admixture is also directed through a second filter, which may be an ultrafilter or a plasma filter, which removes unwanted cellular components along with excess fluid. The unwanted components and excess fluid which is filtered from the blood is drawn off into filtrate retention means.

In some embodiments of the invention, the blood is continuously recirculated through the filtering system until a sufficient amount of fluid has been removed and a specified level of desired blood components (i.e., hematocrit level) has been attained. This is determined by monitoring means. Recirculation may be accomplished by mechanical means, such as a roller pump, or may be accomplished manually by, for example, applying alternating force or pressure which may urge the admixture to pass through the filter means continuously. When the blood component level has reached a specified level, the blood is reinfused into the patient. The specific level of desired blood components, or the hematocrit level, is determined by the attending medical personnel in accordance with the patient's particular requirements. In alternative embodiments, the blood is not recirculated. Rather, the blood is passed through an integrated emboli filter and ultrafilter or plasma filter.

When sufficient amounts of excess fluid have been removed, as measured by monitoring means, the filtered blood is ready for reinfusion into the patient. The monitoring means for use in this system may be any means which determines the amount of fluid in the blood being circulated through the system. For example, such a monitor may constantly evaluate the fraction of noncellular fluid volume in the blood by measuring the impedance of blood at a specified frequency using two stainless steel electrodes. Measured conductivity of blood is known to be proportional to the fraction of noncellular fluid volume in the blood. Such conductivity monitors are available on the market (e.g., Sedatelec, Chemin des Muriers, Irigny, France).

Filters which can be used in the invention to purify blood are those which have the capability of trapping unwanted particles of any particular size. For example, an ultrafilter may be used which is a conventional membrane separator having a pore size ranging from about 40,000 daltons to about 400,000 daltons molecular weight cut off. A preferred pore size is about 100,000 daltons. Representative filters are ultrafilters manufactured by Kuraray Company and Asahi Company, both of Japan. However, if larger impurities are to be removed, a plasma filter having a pore size larger than about 400,000 daltons, and up to 0.6 microns, may be preferred. Other filters may be associated with the reinfusion system for assuring complete filtration. For example, an emboli filter may be associated with the reinfusion system to remove any residual air bubbles before the blood is reinfused.

Blood which has been filtered and comprises appropriate levels of blood cellular components and fluid may be collected in blood collection means. The invention, whether highly mechanized or simply configured, is designed to process blood on a real time basis. The filtered blood may be collected in a bag and reinfused by a batch-type process, or the collected blood may be constantly reinfused from the apparatus of the invention. If collected by batch processing, the filtered blood may be collected in a bag and, for example, may be attached to an I.V. pole for reinfusion. Alternatively, the blood may be infused continuously to the patient from a reinfusion line connected to the collection means of the system.

The invention may be configured as a stand-alone unit which can, for example, be wheeled into the operating forum or intensive care unit following surgery. Alternatively, the invention may be configured as a portable system attached to a conventional I.V. pole.

Embodiments of the invention may employ varying degrees of mechanization to accomplish the different steps of blood aspiration, filtration and reinfusion. In more mechanized embodiments, a series of pumps, valves, and blood level detectors may be in electrical and/or mechanical communication with each other such that processing of the blood is fully automated. For example, aspirated blood is filtered through an emboli filter and collects temporarily in a reservoir associated with the emboli filter. Blood level detectors connected to the reservoir measure a high level of blood in the reservoir and a low level of blood in the reservoir. A signal is thus communicated to a recirculation pump when the blood level is high in the reservoir, causing the pump to pump faster. Correspondingly, a signal is sent to the recirculation pump when the level of blood gets too low in the reservoir, and the pump slows or stops. As the blood/washing fluid admixture circulates through a membrane filter, fluid and other waste components are removed. Removal of the filtrate may be increased by a filtration pump associated with the filtrate drainage means.

As the filtered blood exits the membrane filter, a monitor determines the amount of fluid and desired blood components in the blood. If there is an excess of fluid still remaining in the blood, the recirculation continues. However, when the proper amount of fluid has been removed, as determined by the monitor, a signal is sent to valve means which close off the pathway to recirculation and open the pathway to reinfusion. The blood is filtered once more of air bubbles and is monitored. If no air bubbles exist, a signal is sent to a reinfusion valve which then opens allowing the filtered blood to be reinfused into the patient. The reinfusion valve may also be in communication with the blood level detectors of the reservoir such that if the blood level in the reservoir is too low, the reinfusion valve will not open. A pump on the reinfusion line may be substituted for or may operate in conjunction with the reinfusion valve to infuse blood back to the patient.

The invention may include means for maintaining consistent filtration of the blood by the ultrafilter or plasma filter. That is, filtration means is provided in the system for removing excess fluids and smaller solutes from the aspirated blood without significant decrease in the filtration rate. The filtration means includes two chambers separated by a porous membrane. A circulation chamber serves as a passageway for circulation of blood; a filtration chamber serves to collect filtered fluids and solutes which pass through the porous membrane. Cellular elements of blood cannot pass through the membrane pores because they are larger than the pore size of the membrane. However, cellular elements may become deposited or trapped on the membrane surface or in the pores which decreases the filtration rate. Means associated with the filtration chamber urge fluid from the filtration chamber through the porous membrane and into the circulation chamber to clear the membrane pores of solids which have accumulated and have thus prevented proper filtration. This process may be referred to as "reverse filtration."

Embodiments for postsurgical use provide means for controlling negative pressure in the drainage tubing, which is implanted in the closed wound site to drain blood from the area. By controlling the negative pressure in the drainage tubing, blood may be aspirated without introduction of air into the system. This has the obvious advantage of reducing air emboli, and it further lessens protein denaturation as a result. Postsurgical embodiments may be mechanized to varying degrees, as described above for intraoperative embodiments, or may be fairly simple and manually operated. Such embodiments are easy to handle, are less expensive, and are less subject to mechanical failure.

BRIEF DESCRIPTION OF THE DRAWINGS

In the drawings, which illustrate what is currently considered to be the best mode for carrying out the invention.

DETAILED DESCRIPTION OF THE ILLUSTRATED EMBODIMENTS

Figure 1:
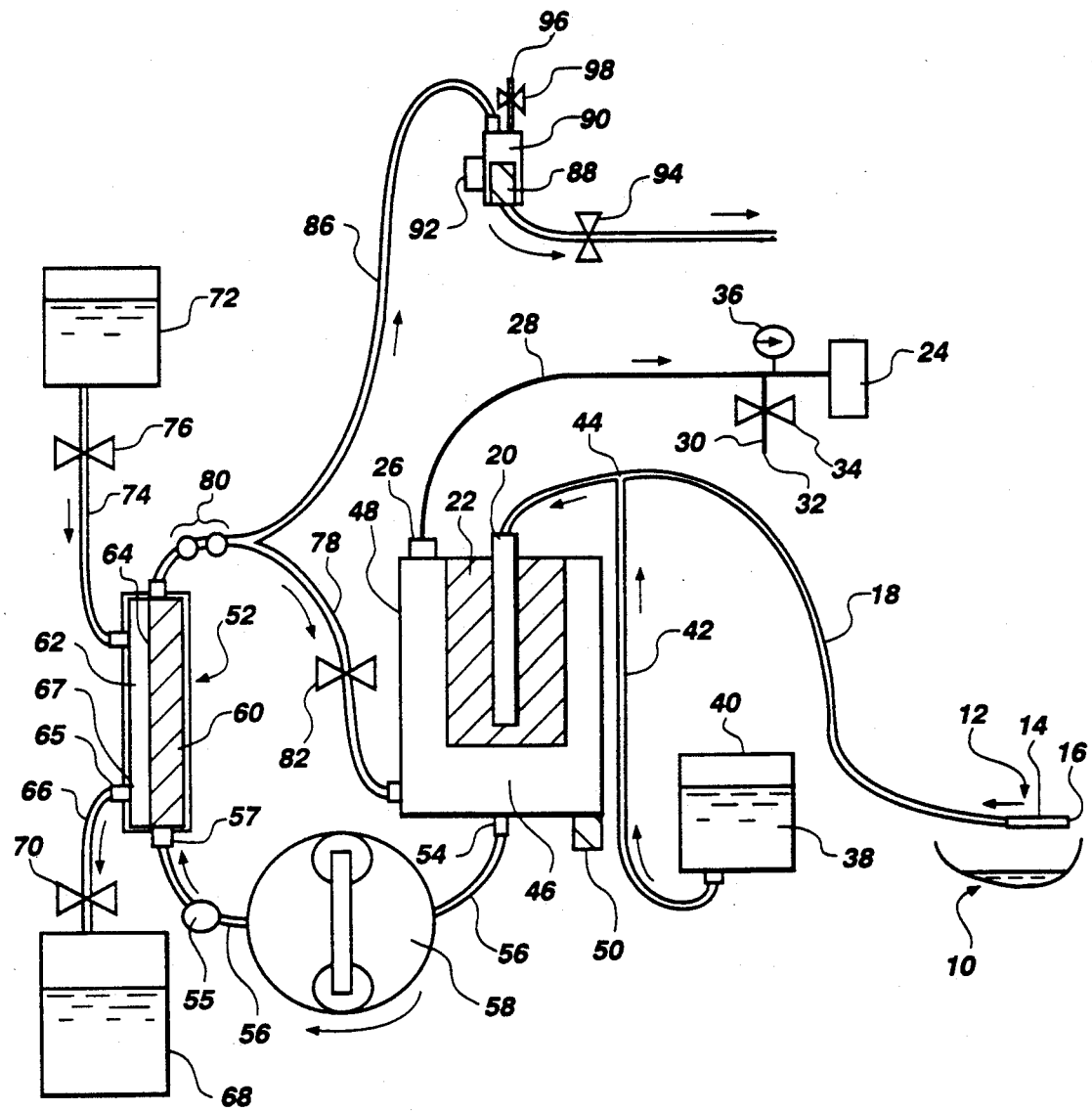
FIG. 1 is a schematic diagram illustrating an autologous blood recovery system having reverse filtration capabilities.

In FIG. 1, the wound site associated with the patient from which blood is aspirated is represented generally at 10. Blood is aspirated from the wound site 10 by aspiration means 12 which includes a handle 14 having a tip 16. The tip 16 of handle 14 is placed in contact with the blood exiting the wound site 10 to effect aspiration. The aspiration means 12 is connected to suction tubing 18 which forms a passageway for blood aspirated from the wound site 10. Suction tubing 18 is connected to the inlet port 20 of emboli filter 22.

Aspiration is achieved by means of negative pressure which is supplied by a vacuum source 24 to the emboli filter 22. Sources of vacuum are commonly found in operating fora and recovery rooms. The vacuum source 24 is associated with the emboli filter 22 at vacuum connector means 26 by a vacuum line 28. An amount of pressure is supplied to the system to draw blood from the wound site 10 into the emboli filter 22; the required level of pressure is between about −80 mm Hg and −160 mm Hg. The pressure level should not exceed about −200 mm Hg.

Regulation of the level of negative pressure associated with the emboli filter 22 may be performed by any number of appropriate means known in the art. FIG. 1 illustrates one means of vacuum regulation in which a tube 30, interconnected to the vacuum line 28, is open at one end 32 to atmosphere. Clamp means 34 are attached to tube 30 to adjustably open and close tube 30 to atmosphere. The level of pressure, as indicated by pressure indicator 36, may therefore be regulated by adjusting clamp means 34 to reduce the level of negative pressure.

Filtration and treatment of aspirated blood is optimized by its admixture with a suitable fluid. A particularly suitable fluid for admixture with the aspirated blood is normal saline or Ringer's Solution. An appropriate amount of anticoagulant may be added to the washing fluid to reduce clotting in the blood. Washing fluid 38 may be introduced into the aspirated blood prior to entering the emboli filter 22, as shown in FIG. 1. Alternatively, washing fluid 38 may be admixed with blood after the blood has been filtered through the emboli filter 22.

Washing fluid 38 is contained in washing fluid retainer means 40 and is introduced for admixture with aspirated blood through washing fluid line 42. Washing fluid retainer means 40 may be any conventional flexible plastic bag for fluid retention. Washing fluid line 42 joins with suction tubing 18 at conjunction point 44, and blood and washing fluid 38 are admixed together at that juncture. The conjunction point 44 may be a Y-connector joining the suction tubing 18 and washing fluid line 42 together.

The amount of impurities removed from the blood is maximized as the proportion of washing fluid 38 relative to aspirated blood increases. Optimally, the ratio of washing fluid 38 to aspirated blood should be about one to two. In the present invention, optimal proportions of washing fluid 38 to aspirated blood are achieved by maintaining the washing fluid retainer means 40 approximately two feet in relative height below the aspiration means 12. Thus, when negative pressure is applied to the emboli filter 22 via the vacuum source 24, and the tip 16 of the handle 14 is positioned in a pool of blood at the wound site 10, negative pressure (i.e., suction) is simultaneously applied to the blood and to washing fluid line 42, and washing fluid 38 is drawn through washing fluid line 42 into suction tubing 18.

When no blood is present at the wound site, the level of negative pressure exerted on suction tubing 18 decreases. As negative pressure decreases, less negative pressure is applied to the washing fluid line 42. Because the washing fluid retainer means 40 is positioned about two feet below the relative height of the aspiration means 12, the amount of pressure exerted on the washing fluid line 42 will be inadequate to draw washing fluid 38 into suction tubing 18. Thus, proportionately less washing fluid 38 is drawn into the suction tubing 18. It can be appreciated, therefore, that when the washing fluid retainer means 40 is positioned about two feet below the relative height of handle 14, washing fluid 38 is thereby drawn into the suction tubing 18 in proper proportion to the amount of blood being aspirated. It can further be appreciated that by suitably adjusting the flow resistance in the washing fluid line 42 with respect to the flow resistance in the suction tubing 18 and aspiration means 12, the flow rate of washing fluid 38 may be adjusted to any desired ratio. Such resistance may be achieved by varying the diameter of the washing fluid line 42 or by varying the relative heights of the washing fluid retainer means 40.

Figure 9:
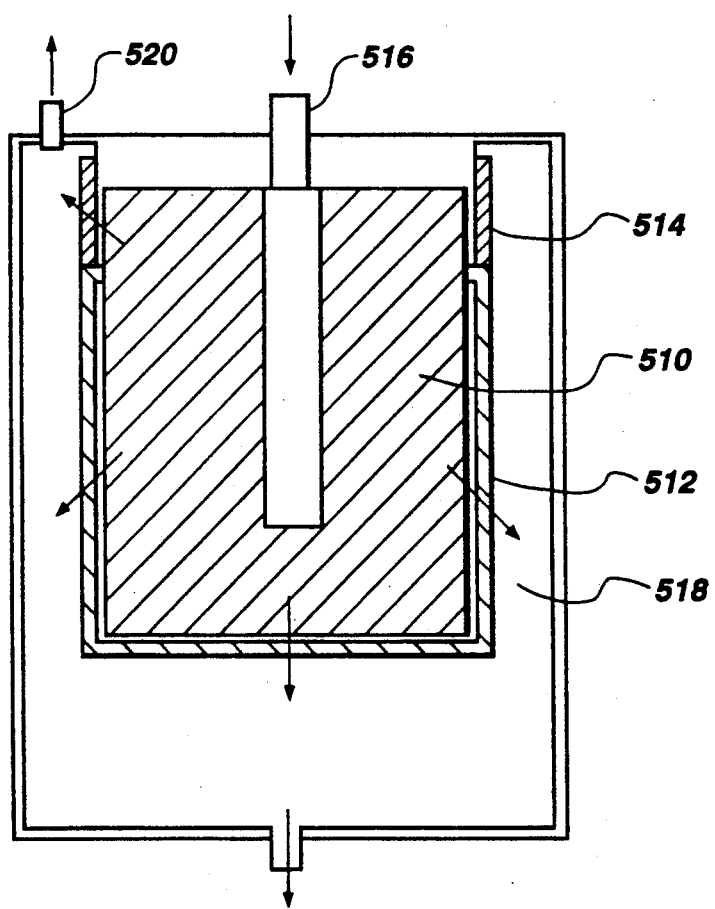
Figure 10:
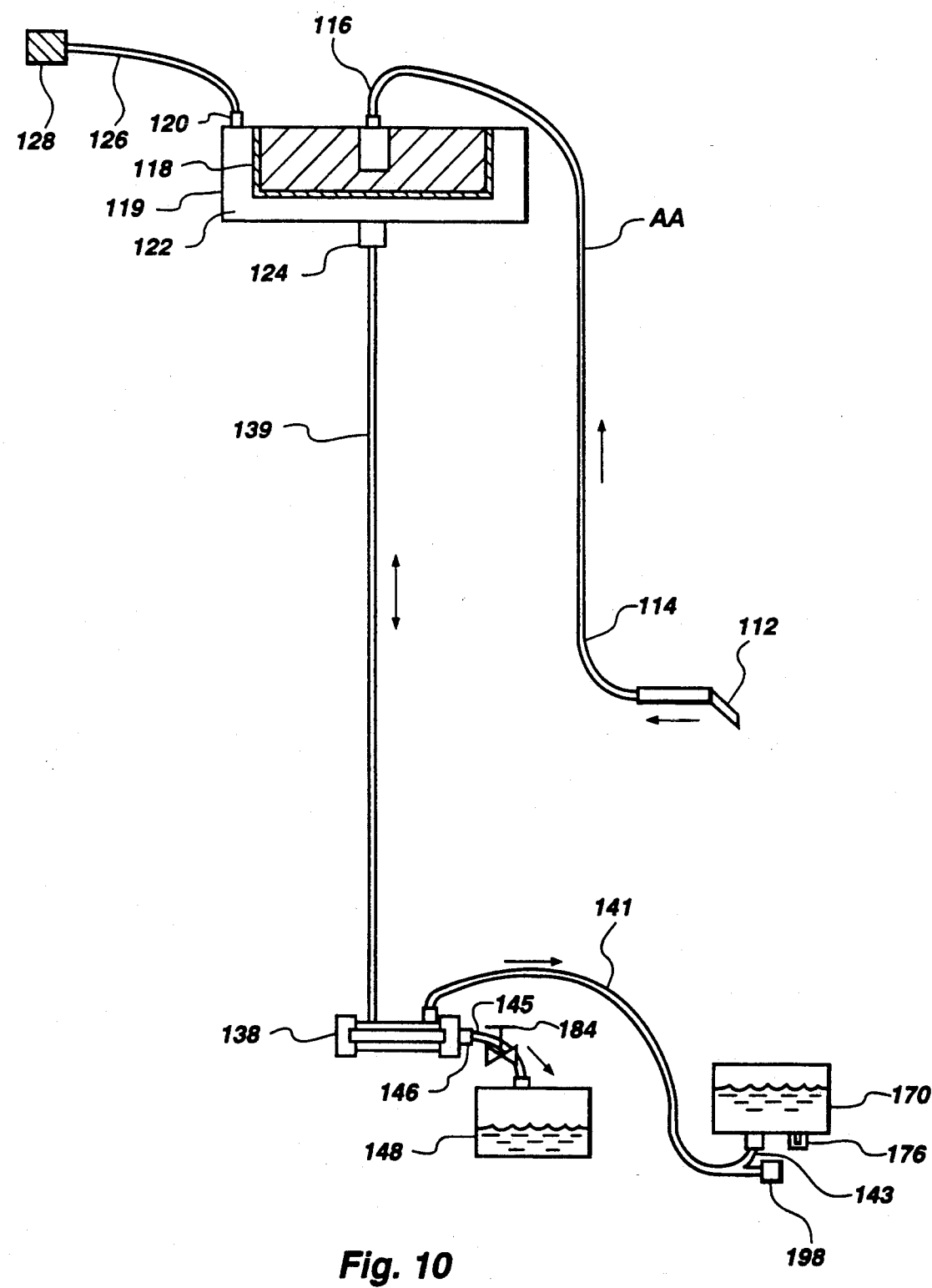
Figure 11:
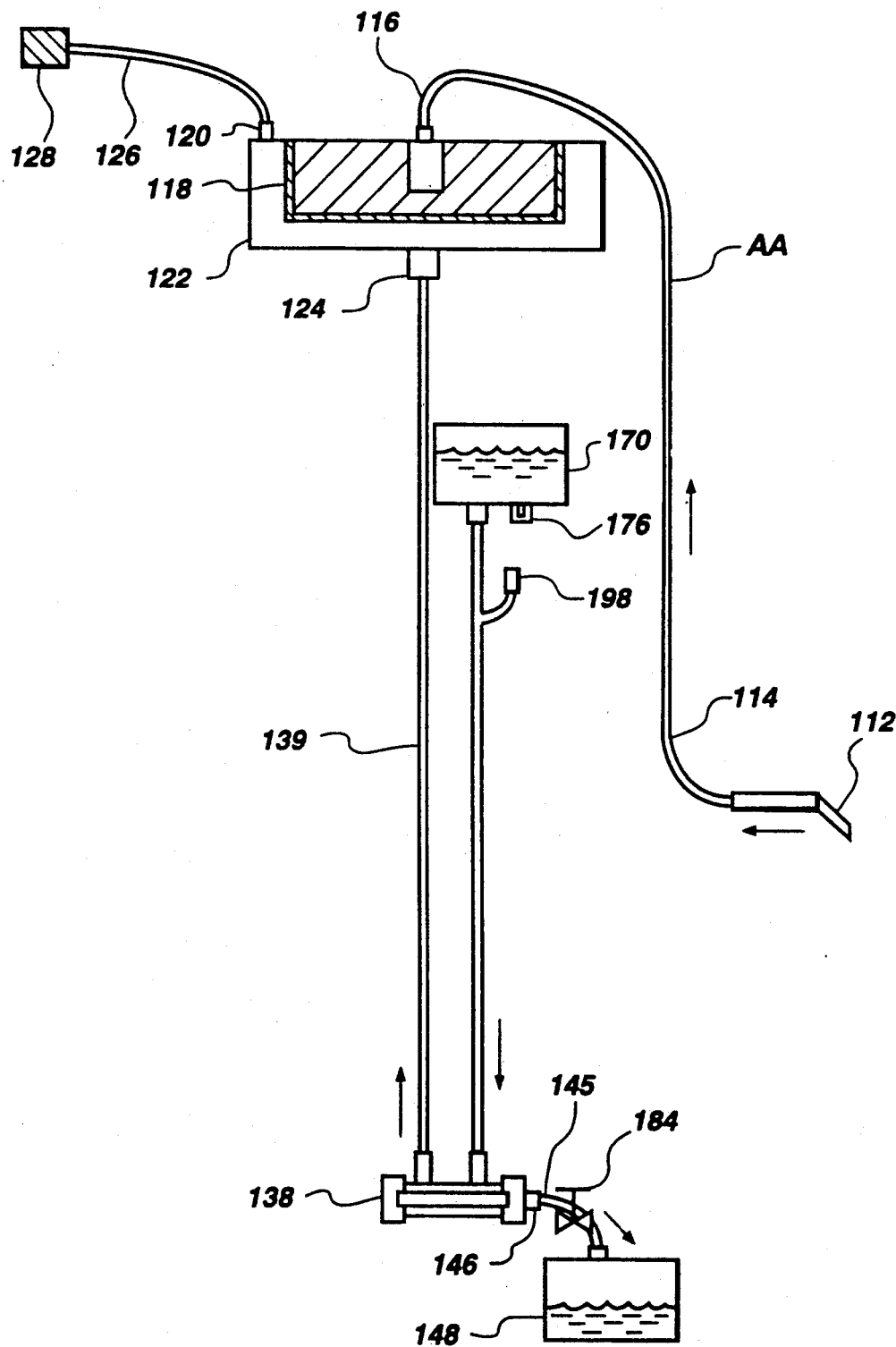
Figure 12:
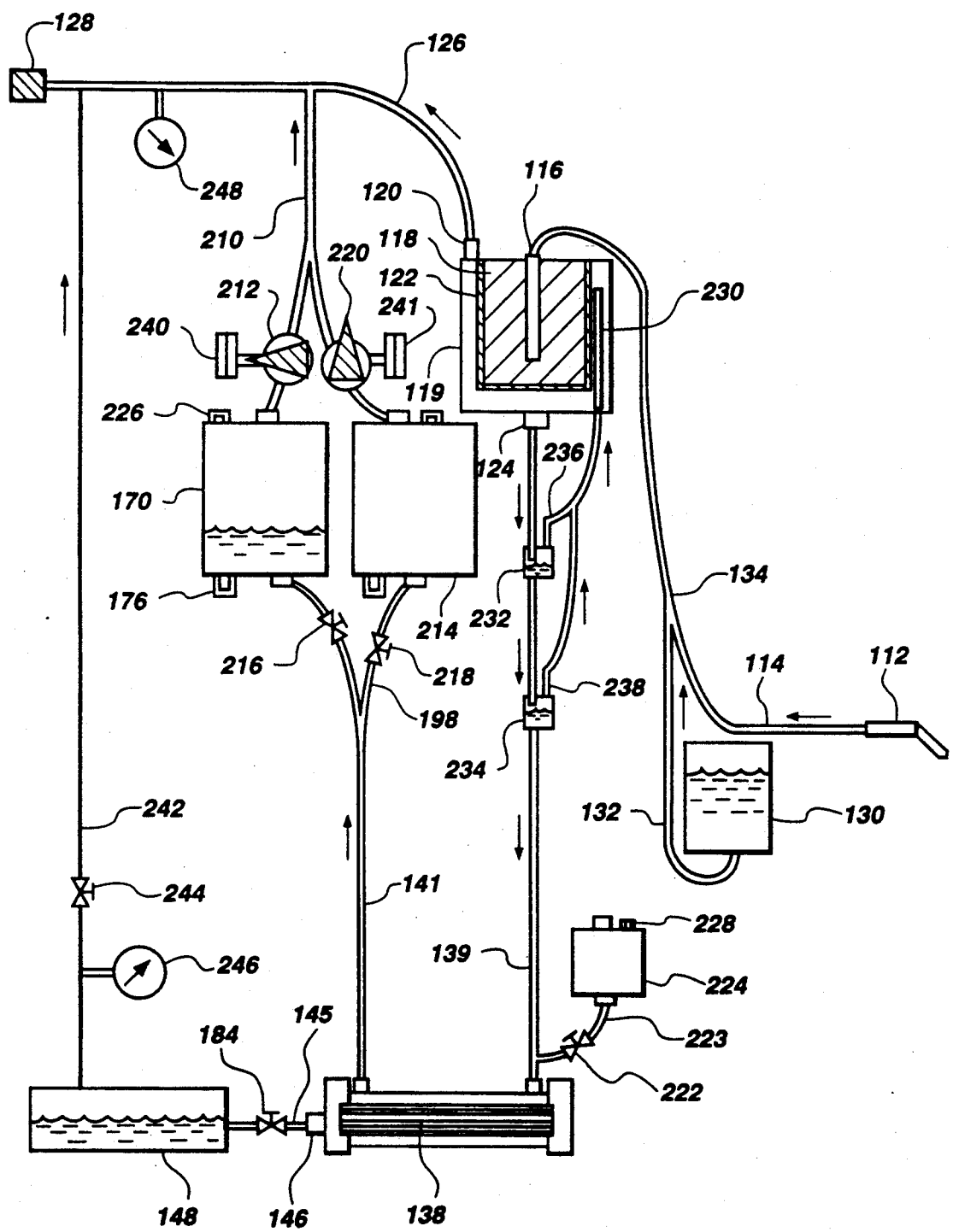
Figure 13:
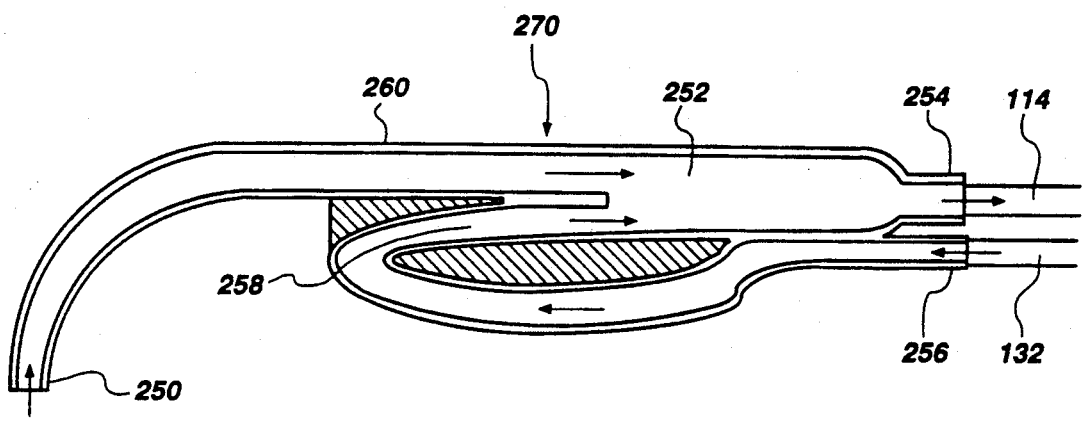

Admixed washing fluid 38 and aspirated blood enter into the emboli filter 22 at inlet port 20. The emboli filter 22 may be of any type or configuration which filters out air bubbles and large particulates from the aspirated blood. A particularly suitable emboli filter for use in the invention is that disclosed by FIG. 9 in copending application Ser. No. 525,536. Blood is filtered through the bottom portion of emboli filter 22, and large impurities, typically greater than 40 microns, are filtered out. Blood collects in a reservoir 46 formed between the emboli filter 22 and the outer casing 48 in which the emboli filter 22 is positioned. Air bubbles which are separated out by the emboli filter 22 are drawn off by the negative pressure applied to the emboli filter 22. The vacuum source 24 further aspirates air which may exist in the blood retained in the reservoir 46.

The level of blood in the reservoir 22 is detected by detection means 50 located at the bottom of the reservoir 46. The detection means 50 may be any device which is capable of determining fluid levels, and may particularly be an ultrasonic sensor which continuously measures the level of blood in the reservoir 46. Examples of such ultrasonic sensors are those made by Zevex, Inc. (Salt Lake City, Utah) or MinnTech, Inc. (Minneapolis, Minn.).

Continuous on-line removal from the blood of impurities and excess water is provided in the present invention. Once the excess fluid has been removed from the blood, the blood may be reinfused to the patient. Continuous on-line filtration and purification is achieved by recirculating the blood from reservoir 46 through a porous membrane filter 52, and back to the reservoir 46 until a sufficient amount of excess fluid has been removed.

Blood exits the reservoir 46 by reservoir outlet 54 and enters into conduit 56 which interconnects between the outer casing 48 and the membrane filter 52. Means for urging the blood along conduit 56, such as recirculation pump 58, may be associated with the conduit 56. Means other than a roller pump, as shown, may be used including electromechanical means and gravity. Pressure sensing means 55 may be associated with conduit 56, and is positioned along conduit 56 between the recirculation pump 58 and the membrane filter 52. The pressure sensing means 55 may either be positioned proximate the recirculation pump 58, or may be positioned proximate the inlet 57 of the membrane filter 52, as shown. The pressure sensing means 55, as described more fully below, monitors the pressure within conduit 56 and may signal the recirculation pump 58 to operate faster or slower in response to increased or decreased fluid pressure within conduit 56, respectively.

Blood enters the membrane filter 52 where smaller solutes and excess fluid are further filtered from the blood. Membrane filter 52 may be any conventional membrane-type separator with a pore size ranging from 40,000 daltons to 400,000 daltons molecular weight cut off. Such filters are known in the art as ultrafilters. It may be preferable to use a membrane with a pore size not exceeding 100,000 daltons. However, if larger size impurities are to be removed, a filter having a pore size greater than 400,000 daltons, or a plasma filter having a pore size of 0.6 micron (a few million dalton molecular weight cut off) can be used.

The membrane filter 52 is generally configured with two differentiated regions for circulating fluid, those regions being separated by a membrane. Thus, the membrane filter 52 may, for example, include two similarly shaped and sized chambers separated by a membrane. Alternatively, the membrane filter 52 may comprise a plurality of hollow tubules for blood circulation positioned within a conduit through which washing fluid circulates. Many configurations may be suitable.

As illustrated by FIG. 1, the membrane filter 52 includes a circulation chamber 60 and a filtration chamber 62 which are positioned adjacent to each other and which are separated by a porous membrane 64. Blood from conduit 56 enters the circulation chamber 60 and is subjected to removal of excess fluid and solutes through porous membrane 64. Filtration is accomplished by providing flow constriction means 65 at outlet 67 of the membrane filter 52 which provides a transmembrane pressure differential across the porous membrane 64. Excess water and solutes, referred to hereinafter as "filtrate," are collected in the filtration chamber 62 of the membrane filter 52. Accumulated filtrate exits the filtration chamber 62 by conduit 66 and enters into filtrate retainer means 68. Filtrate retainer means 68 may be any conventional collapsible plastic bag directed to fluid retention. Valve means 70 are associated with conduit 66 for preventing flow of filtrate therethrough.

The porous membrane of a membrane filter is typically subject to clogging as a result of particulate matter (e.g., proteins and blood cells) becoming lodged in the pores and on the surface of the membrane. Therefore, although filtration takes place at a sufficient level at the beginning of the filtration process, filtration eventually slows or may even stop because the pores become clogged. Under such conditions, conventional membrane filters must be replaced. Replacement of the membrane filter is understandably difficult if not impossible during a filtration procedure. Therefore, the membrane filter 52 illustrated in FIG. 1 is designed to clear the pores of the membrane 64 so that filtration may continue at a consistent level throughout the filtration procedure, as will be explained in more detail hereinafter.

To clear the membrane 64, valve means 70 may intermittently close to prevent filtrate from entering or exiting the filtrate retainer means 68 through conduit 66. Simultaneously, valve means 76, associated with conduit 74, is opened to allow flow of fluid through conduit 74. Valve 70 and valve 76 may be interconnected by mechanical or electrical means so that when one valve is open the other valve remains closed. Fluid from a fluid retainer bag 72 enters into the filtration chamber 62 via conduit 74. Fluid may be urged from the fluid retainer bag 72 by mechanical means (not shown) or by raising the fluid retainer bag 72 above the membrane filter 52 to provide flow by gravity. Fluid entering the filtration chamber 62 passes through the porous membrane 64 and forces particulate matter out of the pores into the circulation chamber 60. This event may be termed "reverse filtration." After a period of reverse filtration, valve means 76 is closed to prevent fluid from flowing out of fluid retainer bag 72 into the filtration chamber 62. Simultaneously, valve means 70 is opened so that the filtration process may begin again. The operative modes of filtration and reverse filtration are explained more fully hereinafter.

Filtered blood exits the circulation chamber 60 and enters into conduit 78. Monitor means 80 are associated with conduit 78 and are positioned proximate the membrane filter 52. The monitor means 80 monitors whether the appropriate amount of fluid has been removed from the blood prior to reinfusion to the patient The monitor means 80 may take a number of forms known to those skilled in the art. As suggested by FIG. 1, the monitor means 80 may be a conductivity monitor for detecting cellular volume fraction (e.g., erythrocyte count) of the blood exiting the membrane filter 52. The conductivity monitor constantly measures the conductivity of blood at a specified frequency using two stainless steel electrodes (not shown) at the outlet of the membrane filter 52 Such conductivity monitors are available, for example, from Sedatelec, Chemin des Muriers, Irigny, France. These electrodes supply a current of ten micro amperes to the blood at a frequency of five thousand hertz. Measured conductivity of blood is known to be proportional to its noncellular volume fraction.

Figure 4:
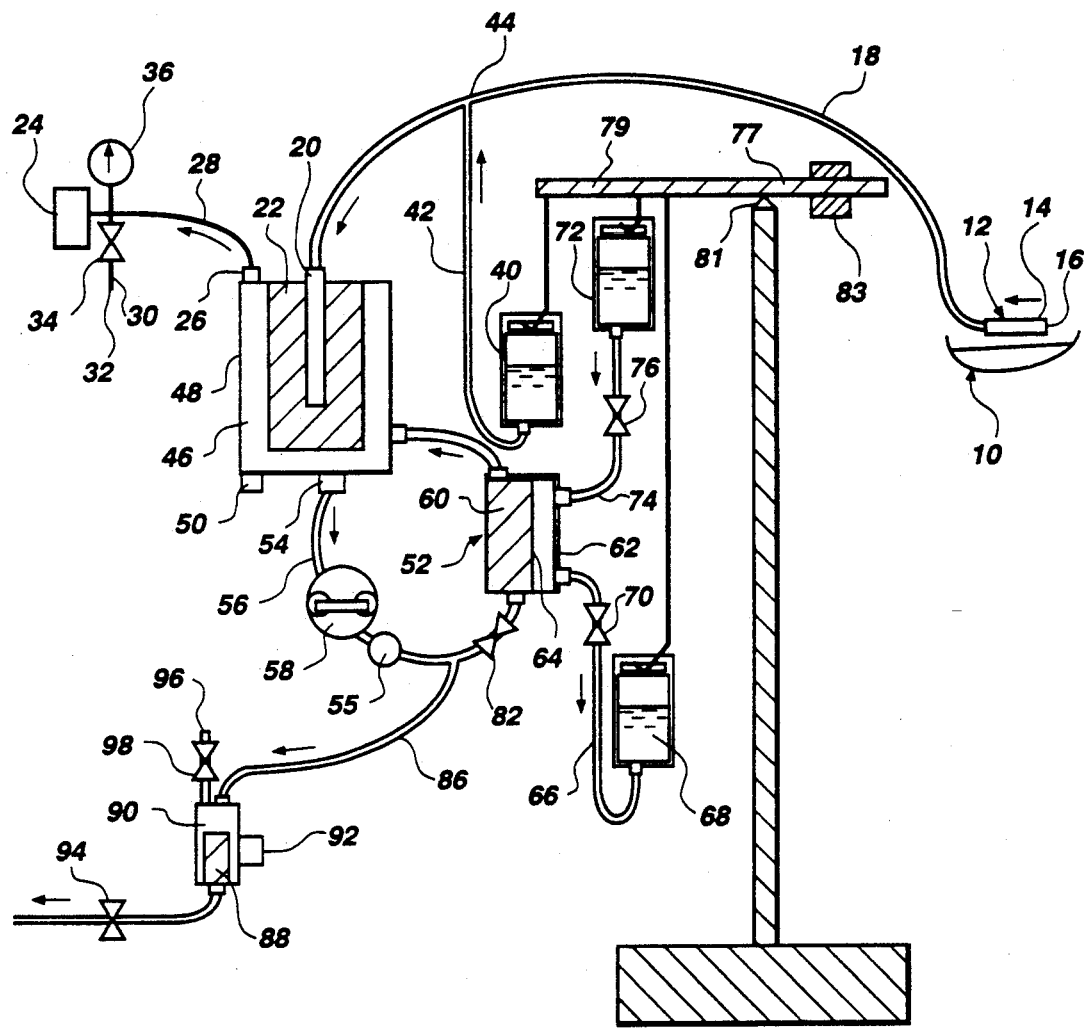
FIG. 4 is a schematic diagram illustrating a monitoring means for determining fluid removal from the blood.

Alternatively, the monitor means 80 may operate to determine the amount of fluid which has been introduced into the apparatus relative to the amount of fluid which has been removed via filtration. Monitor means 80 of this type may take several forms. FIG. 4 illustrates one method in which the washing fluid retainer means 40, fluid retainer bag 72, and filtrate retainer means 60 are associated with a weighing balance 77. The balance may comprise a balance arm 79 positioned relative to a fulcrum 81 or balance point. A counterbalance 83 or measuring device may be positioned in opposition to the fluid containers 40, 72 and 68.

The balance is calibrated to some value, such as zero. Thus, if fluid, introduced from the washing fluid retainer means 40 or the fluid retainer bag 72, is still circulating with blood through the apparatus, the total weight of fluid in the washing fluid retainer means 40, fluid retainer bag 72 and filtrate retainer means 60 will be less than the original sum of fluid and a negative value will be registered by the counterbalance 83. When such a deficit of fluid occurs, filtration will continue until substantially all of the fluid has been removed, as measured by balance 77. Many various types of balances, well known to those skilled in the art, may be used. Further, any means by which fluid amounts may be measured would be suitable for use in the invention.

As excess fluid is filtered out of the blood by the membrane filter 52, the cellular volume fraction (e.g., hematocrit) will increase. If the hematocrit level of the blood is below a specified value, or, if an insufficient amount of fluid has not been removed from the circulating blood, the blood continues through conduit 78 and reenters reservoir 46. The blood is recycled again through conduit 56, through the membrane filter 60 and through conduit 78 as described previously.

Once the monitor means 80 detects that the cellular volume fraction has reached a specified level, or detects that the appropriate amount of fluid has been removed from the blood, recirculation valve means 82 closes thereby preventing blood from continuing to be recycled through the system. Simultaneously, valve means 70 closes preventing further filtration. As valve means 70 closes, valve 76 opens and reverse filtration occurs. The recirculation valve means 82 may be a three way shunt valve which intermittently allows blood to flow through the recirculation pathway, and intermittently occludes that pathway thereby allowing the blood to enter the reinfusion line 86.

Blood shunted into reinfusion line 86 for ultimate reinfusion into the patient is filtered once more through a second emboli filter 88. The filtered blood is also subjected to a bubble trap 90 for assuring that all emboli are removed. The blood is measured by blood level detector means 92 to determine the presence of air. If any air is detected, valve means 94 closes the reinfusion line 86 thereby preventing blood from being reinfused back to the patient. If, however, no air is detected in the blood, valve means 94 is opened and blood is reinfused back to the patient. Two other conditions must also be present in order for valve means 94 to be opened and for reinfusion to take place: First, the level of blood in reservoir 46 must be above a certain level as detected by detection means 50 associated with the reservoir 46, and second, the cellular volume fraction of recirculating blood must be equal to or greater than a specified value as monitored by the monitor means 80. Those skilled in the art will understand that detection means 50, monitor means 80, recirculation valve means 82, and valve means 94 are intercommunicationally linked.

Figure 2:
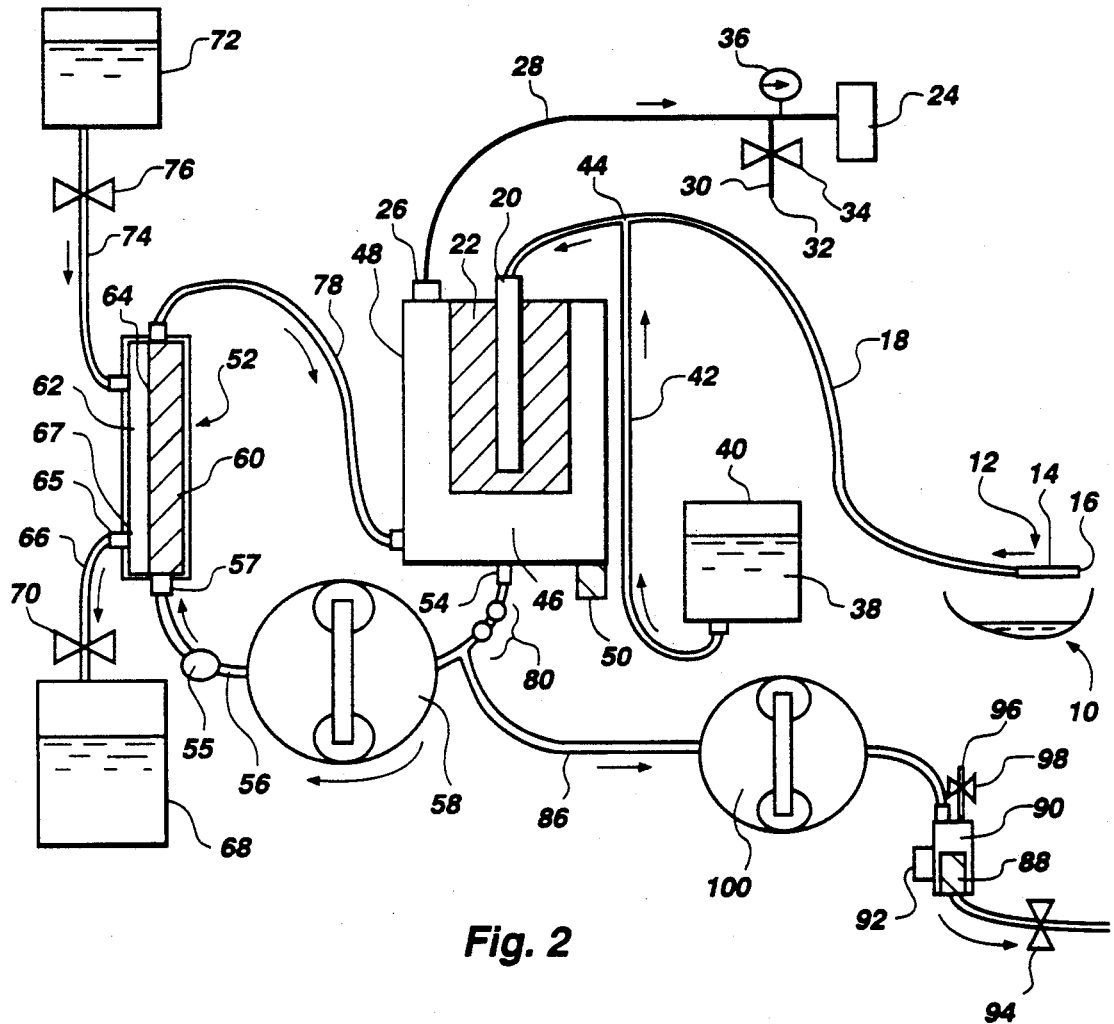
FIG. 2 is a schematic diagram illustrating an alternative means of reinfusing blood to the patient.

In an alternative embodiment, as illustrated by FIG. 2, reinfusion of blood to the patient is accomplished by a reinfusion pump 100 associated with the reinfusion line 86. In this embodiment, recirculation valve means 82 and valve means 94 are eliminated. As previously described, blood is aspirated from the wound site 10 and enters emboli filter 22 where it is filtered of large particulates and emboli. The blood filters into reservoir 46 and circulates to the membrane filter 52 through conduit 56. After being filtered by the membrane filter 52, the blood returns via conduit 78 to reservoir 46 for recirculation.

In this embodiment, monitor means 80 is positioned proximate the blood reservoir outlet 54, and blood exiting the reservoir 46 is constantly monitored for attainment of a specified cellular volume fraction or sufficient removal of excess fluid. The blood continues to recirculate through the system until the specified blood content is attained. When the monitor means 80 senses that the specified blood content level has been reached, recirculation pump 58 slows or stops, blood recirculation slows or stops, and reinfusion pump 100 begins to operate. Blood is thereby urged into reinfusion line 86 by the negative pressure created in the reinfusion line 86 by reinfusion pump 100. The blood is filtered once more through a second emboli filter 88 and bubble trap 90. When the blood is assured to be free of air, as detected by blood level detector means 92, reinfusion of blood into the patient commences.

As illustrated by FIG. 2, the reinfusion line 86 may be interconnected with conduit 56 which interconnects between the reservoir 46 and the membrane filter 52. Alternatively, the reinfusion line 86 may interconnect with conduit 78 as illustrated in FIG. 1. It is only important that monitor means 80 be positioned in proximity to reinfusion line 86 to detect the proper level of cellular volume fraction or removal of excess fluid prior to reinfusion of blood.

Figure 3:
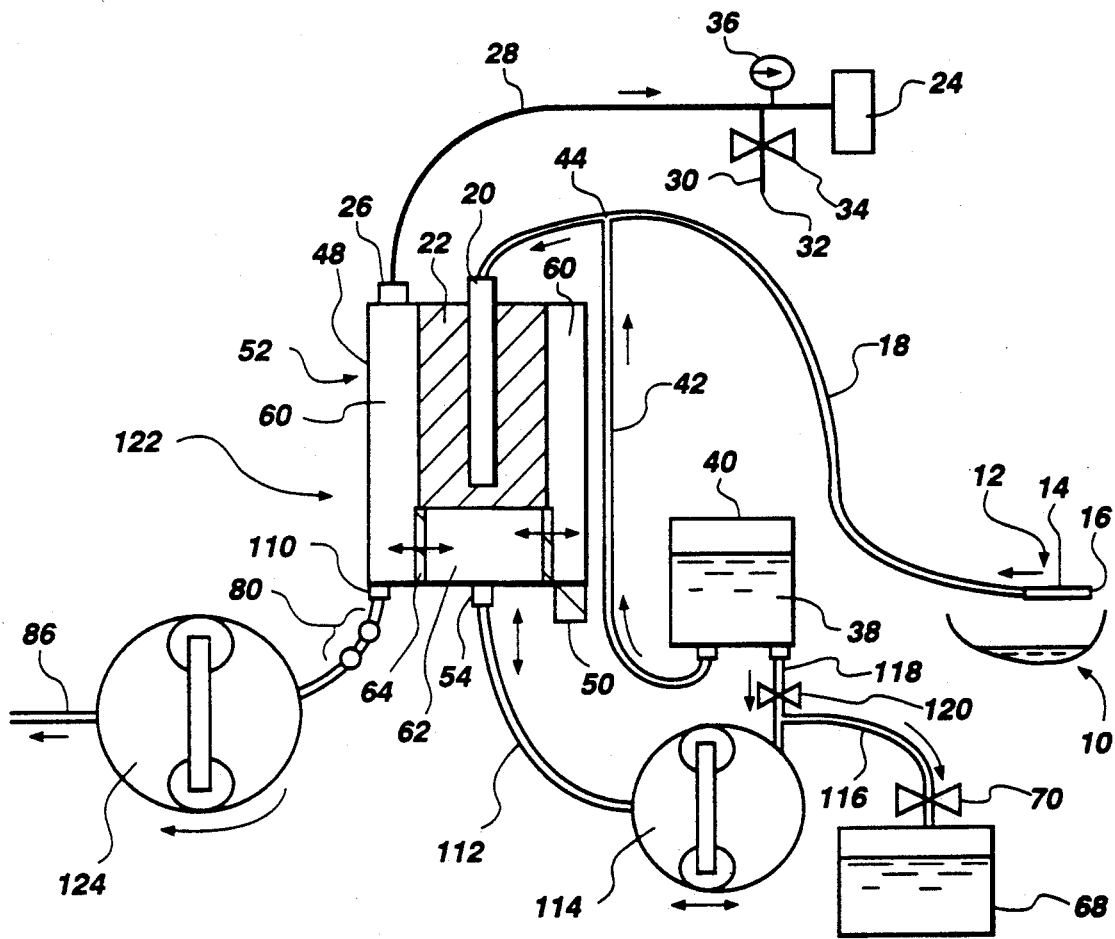
FIG. 3 is a schematic diagram illustrating reverse filtration means in association with an integrated filter system.

FIG. 3 illustrates an alternative embodiment to that illustrated in FIGS. 1 and 2 in which the emboli filter 22 and membrane filter 52 are integrated as a single unit housed within the outer casing 48. As with the previously described embodiments, aspiration means 12 are provided for aspirating blood from the wound site 10; washing fluid 38 is retained in washing fluid retainer means 40; the washing fluid 38 is introduced into admixture with aspirated blood by increasing negative pressure in the suction tubing 18 produced by a vacuum source 24 associated with the emboli filter 22; and admixed blood and washing fluid 38 enters the emboli filter 22 at the inlet port 20 of the emboli filter 22. A vacuum source 24 is associated with the outer casing 48 surrounding the emboli filter 22 by vacuum connector means 26.

In FIG. 3, the membrane filter 52 is integrated with the emboli filter 22 within the outer casing 48. The emboli filter 22 is capable of filtering out macroaggregates which are larger than about 40 microns. The membrane filter 52 has a pore size of about 40,000 daltons to about 0.6 microns. The membrane filter 52 is positioned relative to the emboli filter 22 so that as blood exits the emboli filter 22, it encounters the circulation chamber 60 of the membrane filter 52. As suggested by the schematic of FIG. 3, the membrane filter 52 may encircle the emboli filter 22, and blood flowing through the circulation chamber 60 exits through outlet port 110 formed at the bottom of the outer casing 48. The filtration chamber 62 of the membrane filter 52 is positioned proximate the bottom of the outer casing 48 and the porous membrane 64 surrounds the filtration chamber 62. Other configurations integrating the membrane filter 52 and emboli filter 22 are possible, the aforementioned configuration being merely suggestive. Though not indicated in FIG. 3, a reservoir may also be formed in the outer casing 48 to accumulate filtered blood.

Blood filters through the emboli filter 22 and then through the circulation chamber 60 of the membrane filter 52. Excess fluid and small particulates are separated or filtered out of the blood across the porous membrane 64. The filtrate of excess fluid and particulates is collected in the filtration chamber 62. The filtrate exits the filtration chamber 62 through filtrate conduit 112, and enters into a filtrate retainer bag 68. Mechanical means, such as a filtrate pump 114, urges the filtrate along filtrate conduit 112 to the filtrate retainer means 68.

Filtrate conduit 112 is bifurcated at a point intermediate the filtrate pump 114 and the filtrate retainer bag 68 and forms an efferent line 116 interconnected with the filtrate retainer bag 68, and an afferent line 118 interconnected with the washing fluid retainer means 40. Clamp means 70 are associated with the efferent line 116 to prevent washing fluid from entering into the filtrate retainer bag 68 during reverse filtration. Clamp means 120 are associated with the afferent line 118 to prevent filtrate from entering into the washing fluid retainer means 40 during filtration. It will be understood that when valve means 70 is open, valve means 120 is closed and vice versa.

Under conditions of filtration, filtrate pump 114 moves in a direction to urge filtrate from the filtration chamber 62 of the membrane filter 52 through filtrate conduit 112 and efferent line 116 into the filtrate retainer bag 68. During this time, clamp means 70 is opened to allow filtrate to flow through efferent line 116, and valve 120 remains closed. In response to an indication by monitor means 80 that hematocrit levels are sufficiently high, filtration stops, clamp means 70 closes, clamp means 120 opens, and filtrate pump 114 rotates in the opposite direction to thereby urge washing fluid 38 from the washing fluid retainer means 40 along afferent line 118 and into filtrate conduit 112. Washing fluid 38 urged into the filtration chamber 62 of the membrane filter 52 dislodges debris clogged in the pores of the membrane 64 by forcing washing fluid therethrough. This procedure may be termed "reverse filtration."

When the monitor means 80 indicates that insufficient excess fluid has been removed from the circulating blood, clamp means 120 closes, filtrate pump 114 reverses direction, and clamp means 70 opens so that filtration of the blood may continue again. Notably, although the washing fluid used for performing reverse filtration is illustrated in FIG. 3 as coming from the same washing fluid retainer means 40 which supplies washing fluid 38 for admixture with aspirated blood, a separate fluid retainer means may be used.

It should be noted that when the blood level in the integrated filter 122 is sufficiently low, as measured by detection means 50 positioned proximate the bottom of outer casing 48, filtration stops. At that time, clamp means 70 closes off efferent line 116 and filtrate pump 114 ceases to operate. The reinfusion pump 124 associated with the reinfusion line 86 will also cease to operate thereby preventing reinfusion of blood to the patient. It will be understood by those skilled in the art that when the blood level becomes low in the integrated filter 122, the continuation of filtration and pumping of blood through reinfusion line 86 may introduce air bubbles into the filtered blood. Therefore, reinfusion and filtration must cease. Under conditions when a sufficient amount of blood is aspirated into the integrated filter 122, the cellular volume fraction of the blood is constantly monitored by monitor means 80 positioned proximate the outlet port 110. When a sufficient amount of excess fluid has been removed from the circulating blood, reinfusion pump 124 will begin to function, thereby infusing filtered blood back to the patient through reinfusion line 86. During reinfusion, valve means 70 closes thereby preventing filtration, and valve means 120 opens to allow reverse filtration to take place.

OPERATION OF THE INVENTION

Figure 5:
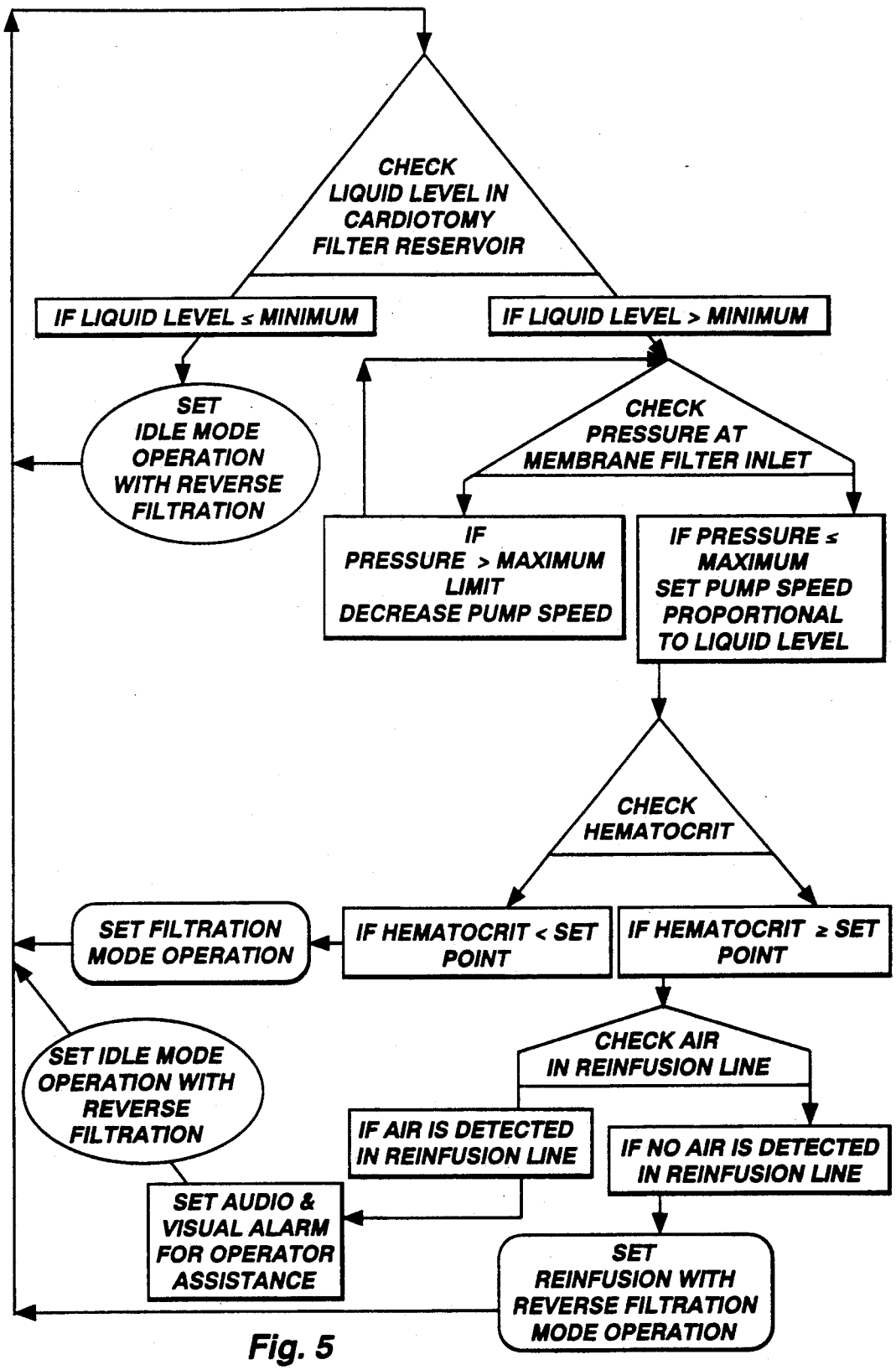
FIG. 5 is a flow chart illustrating operation of the invention in various modes.
Figure 6:
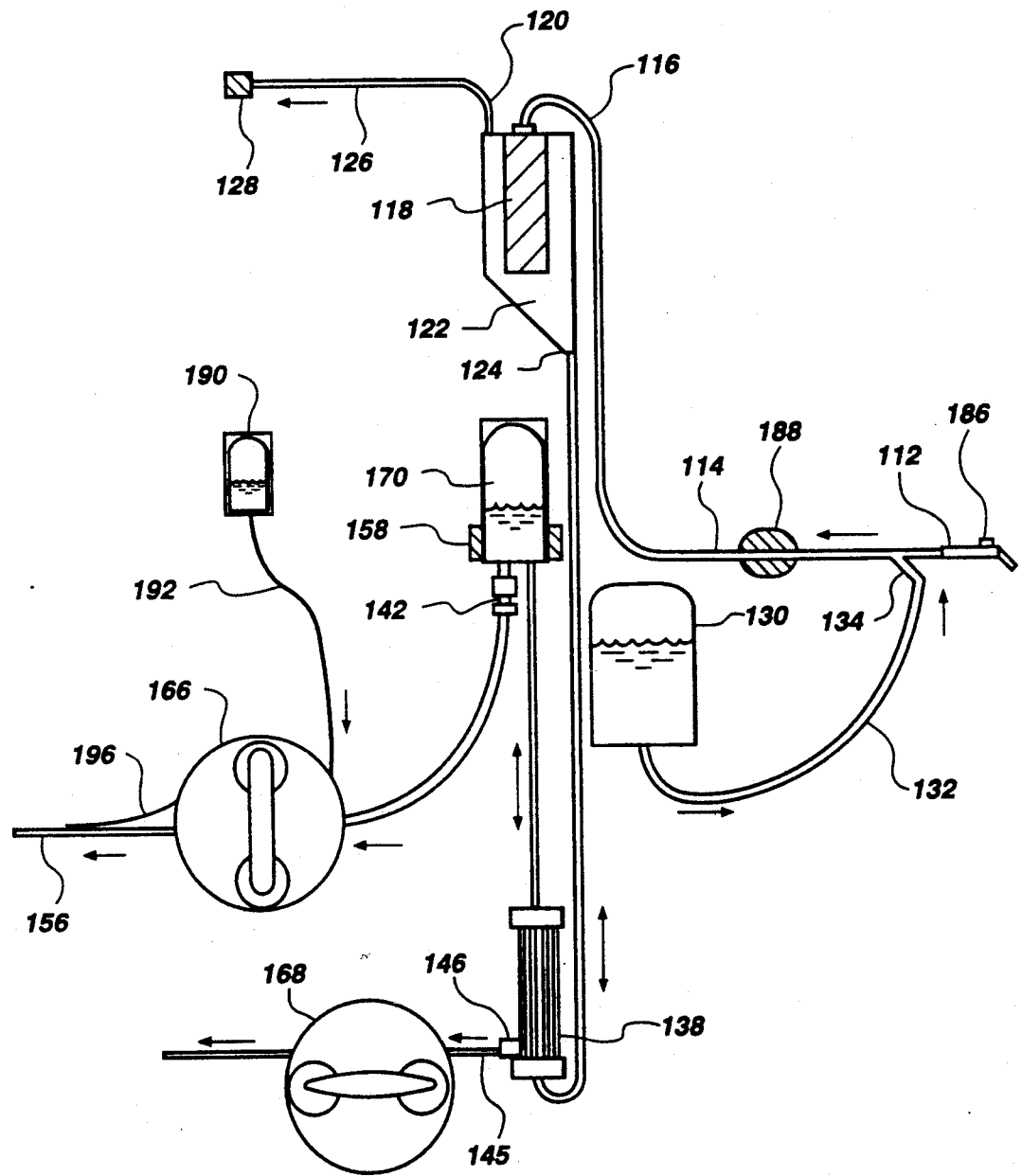
Figure 7:
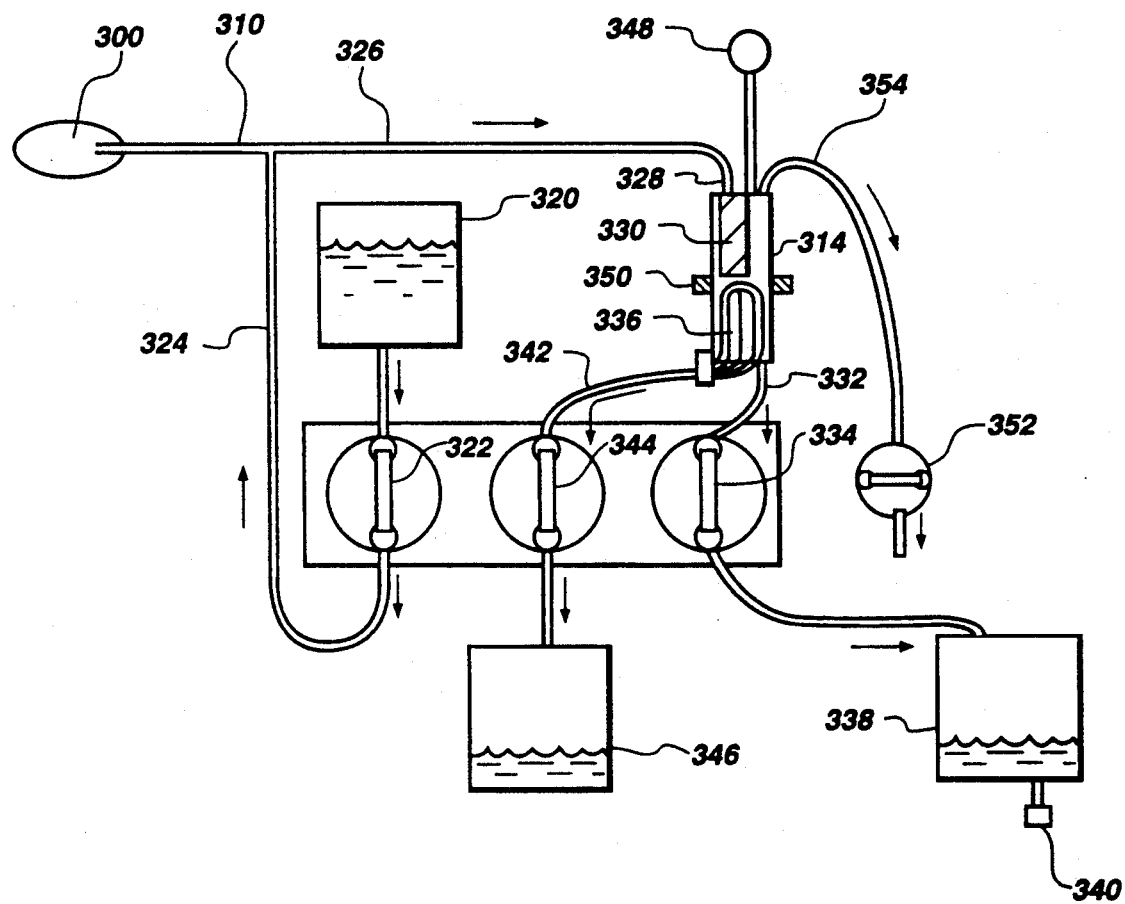
Figure 8A:
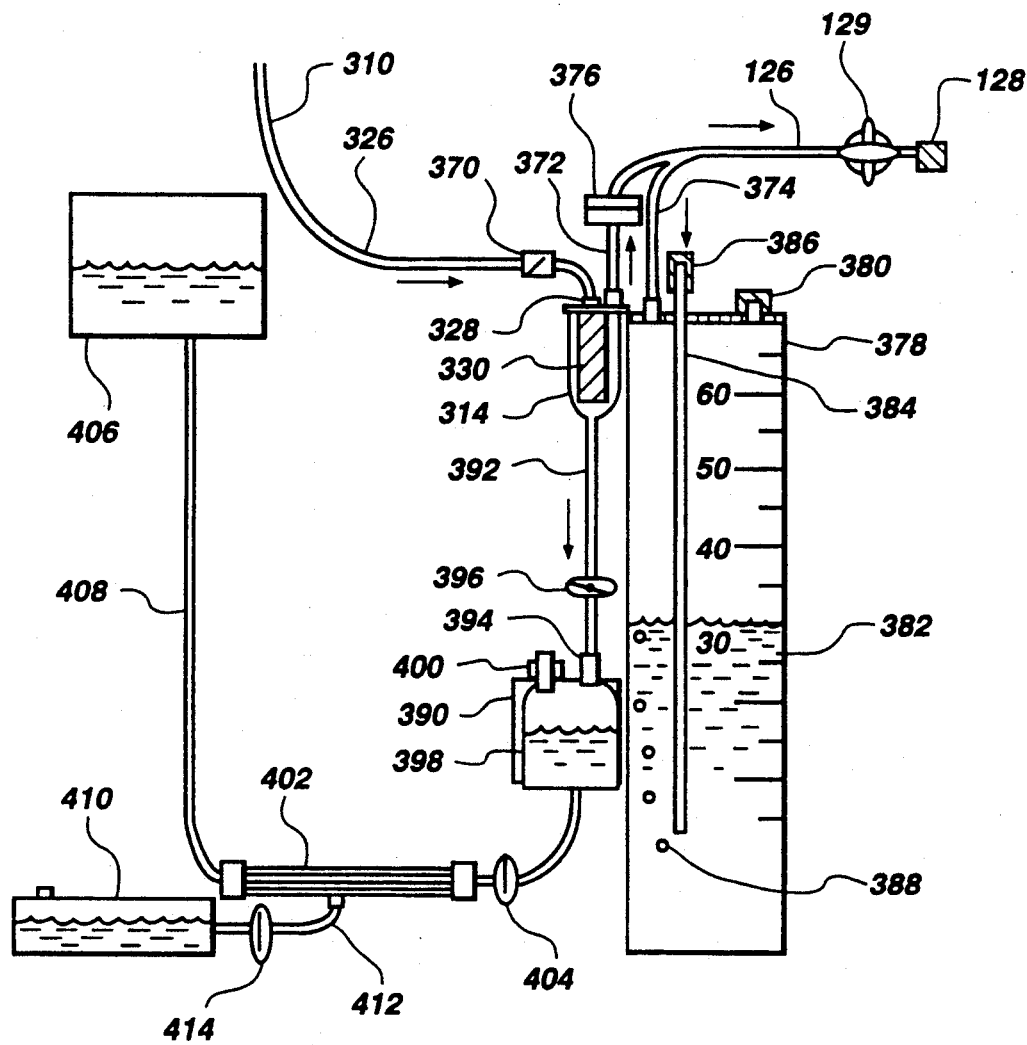
Figure 8B:
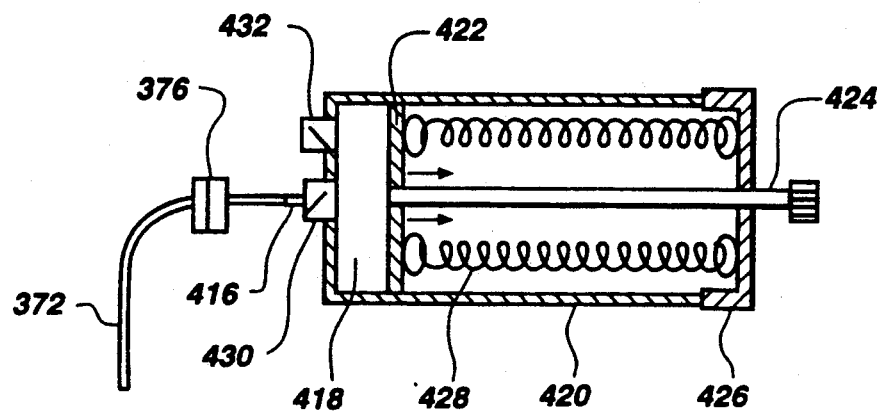

Bleeding during any operation, or during post-operative periods, is typically sporadic. Thus, there may not always be blood circulating in the apparatus, or there may be very little blood circulating therethrough. Therefore, the present invention is designed to operate in essentially three modes: Idling, filtration, and reinfusion. The operation of these three modes is illustrated in the flow chart of FIG. 5.

Idling of the system occurs whenever (1) the fluid level in the reservoir 46 drops below a specified level as detected by detection means 50, (2) the amount of fluid circulating in the system is above the specified level as determined by monitor means 80, and/or (3) air is detected in bubble trap 90. It will be understood by those skilled in the art that the blood level in reservoir 46 cannot fall below a minimum level or air may be introduced into the system. Therefore, under the stated conditions, valve means 76 is open, valve means 70 is closed, recirculation valve 82 is open, and reinfusion valve 94 is closed. Because valve means 76 is open, fluid from the fluid retainer means 72 enters through the membrane filter 52 and circulates through conduit 78, into reservoir 46, through conduit 56, and into the membrane filter 52. Reverse filtration thus takes place.

Fluid continues to circulate through the system until detection means 50 detects that fluid level in the reservoir 46 is above a certain specified level. Usually, the increase in fluid level in the reservoir 46 will be due to blood being aspirated into the system, along with washing fluid 38 from the washing fluid retainer means 40. In the idling mode, the speed of the recirculation pump 58 decreases to a set minimum speed to prevent damage to any blood circulating in the system (i.e., hemolysis) and to avoid clotting of the blood due to stagnation of the fluid.

It is to be noted that when no blood is being aspirated into the system, the apparatus is generally in a reverse filtration mode. As such fluid is always circulating through the system and the introduction of air bubbles into the system is prevented. The system is also self priming at initialization. That is, when the invention is first turned on or initialized, the detection means 50 will determine a lack of fluid in the reservoir 46 and fluid from the fluid retainer means 72 will enter into the system. Thus, the idling mode is initialized from the beginning and will continue until bleeding begins and all other conditions indicate that filtration is required.

Filtration is initiated when the level of fluid in the reservoir 46 is above a specified level, when the monitor means 80 detects that fluid is to be removed from the blood, and when no air is detected in the bubble trap 90. During filtration, valve means 70 is opened, valve means 76 is closed, recirculation valve 82 is opened, and valve means 94 is closed. Blood and washing fluid recirculates through the system and is constantly monitored by monitor means 80. The speed of recirculation pump 58 increases in response to increased levels of fluid/blood in the reservoir 46 as detected by detection means 50, and further in response to a detected increase in pressure within conduit 56 as determined by pressure sensing means 55.

Filtration will continue as long as the monitor means 80 detects that fluid must be removed from the system, and as long as the fluid level in reservoir 46 remains above the minimum specified level. If the fluid level in the reservoir drops below the specified level, the operation mode is converted to idling and reverse filtration will occur. If the fluid level in reservoir 46 is above the minimum specified level, and pressure within conduit 56 is above a specified amount, the pump speed decreases until the pressure within conduit 56 has attained a specified level. If the fluid level in reservoir 46 is above the minimum specified level, and pressure within conduit 56 is below a set maximum level, the pump speed is regulated proportionately to the amount of fluid in the reservoir 46. If monitor means 80 detects that all necessary excess fluid has not been filtered out from the blood, filtration will continue until a required amount of fluid has been removed from the blood.

When monitor means 80 detects sufficient removal of fluid, when the fluid level in the reservoir 46 is sufficiently high, and when no air is detected in bubble trap 90, reinfusion of blood to the patient commences. Valve 70 closes, valve 76 opens, valve 82 remains open, and valve 94 opens. During reinfusion, reverse filtration also takes place. Typically, reinfusion takes place for only a few minutes. During reinfusion, reverse filtration will cause about two to three milliliters of fluid from fluid retainer means 72 to enter into the blood which is being reinfused. The amount of fluid added is not considered to be a significant amount.

Reinfusion continues until the detection means 50 detects that the fluid level in the reservoir 46 drops to the minimum level. At that time, reinfusion ceases and idling commences. As the fluid level in the reservoir 46 rises and the monitor means 80 detects that more fluid needs to be removed, filtration will commence.

It should be noted that if air is detected in the bubble trap 90, an audio and/or visual alarm may advise the attending operator that air has been detected in the second emboli filter 88 and bubble trap 90. The air may then be removed by any conventional method known to those skilled in the art. Particularly, air may be removed by introducing a sterile syringe into vent line 96 associated with the filter 90, opening vent line valve 98, and aspirating the air out.

The reinfusion line may be primed at initialization of the apparatus by momentarily adjusting the monitor means 80 to register that all fluid has been removed from the system. The system will be triggered into the reinfusion mode of operation as long as the level of fluid in the reservoir 46 is sufficiently high. During the brief moment of readjustment of monitor means 80, valve means 94 opens, the recirculation valve 82 closes, valve means 70 closes and valve means 76 opens.

The present invention is directed to filtration and treatment of autologous blood for reinfusion into the patient from which the blood was extracted. The concept may be beneficial to many other applications, however, which involve the filtration or purification of fluids, such as related procedures of hemodialysis, plasma filtration, ultrafiltration and the like. The structure of the invention may be modified to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed:

1. Apparatus for treating autologous blood taken from a patient for reinfusion to the patient comprising:
   suction means for aspirating blood from a wound site;
   conduit means for conducting said aspirated blood from said suction means;
   washing fluid retainer means for retaining washing fluid for admixing with said aspirated blood, said washing fluid retainer means being in fluid communication with said conduit means;
   first filter means for removing emboli and large particulates from said aspirated blood, said first filter means being connected to said conduit means;
   vacuum connector means associated with said first filter means for attachment to a source of vacuum;
   filter casing means for enclosing said first filter means therein;
   detection means associated with said filter casing means for detecting blood levels within said casing;
   second filter means for filtering excess fluids and impurities from said blood, said second filter means being in fluid communication with said first filter means;
   filtrate container means associated with said second filter means for containing said excess fluids and particulates filtered from said blood by said second filter means;
   structure means connectable to said second filter means for providing movement of fluid through said second filter means to effect reverse filtration relative to said second filter means;
   reinfusion means in fluid communication with said second filter means for reinfusing filtered blood to said patient; and
   monitor means positioned proximate said reinfusion means for monitoring blood component levels.

2. The apparatus of claim 1 wherein said second filter means includes a circulation chamber and a filtration chamber, said circulation chamber being in fluid communication with said first filter means, and said filtration chamber being in fluid communication with said structure means for providing reverse filtration.

3. The apparatus of claim 2 wherein said structure means for providing reverse filtration includes fluid retainer means in fluid communication with said filtration chamber for supplying fluid to said filtration chamber, and clamp means associated with said fluid retainer means for selectively preventing said fluid from being supplied to said filtration chamber.

4. The apparatus of claim 2 further comprising means for communicating blood from said first filter means to said second filter means and from said second filter means to said first filter means, said apparatus further including first mechanical means for urging the movement of blood within said means for communicating blood.

5. The apparatus of claim 4 further comprising clamp means connected to said means for communicating blood between said second and first filter means, said clamp means selectively preventing said blood from being communicated between said second and said first filter means through said means for communicating blood.

6. The apparatus of claim 5 wherein said clamp means connected to said means for communicating blood, said detection means, said monitoring means and said first mechanical means are all in electromechanical communication with each other.

7. The apparatus of claim 6 further comprising a third filter associated with said reinfusion means, blood level detection means associated with said third filter for detecting the presence of emboli, and clamp means associated with said reinfusion means for selectively preventing reinfusion of blood to said patient, said clamp means being in electromechanical communication with said clamp means connected to said means for communicating blood, said detection means, said monitoring means, said blood level detection means and said first mechanical means.

8. The apparatus of claim 4 further comprising a third filter associated with said reinfusion means and blood level detection means associated with said third filter for detecting the presence of emboli.

9. The apparatus of claim 8 further comprising second mechanical means associated with said reinfusion means for urging blood therethrough, said second mechanical means being in electromechanical communication with said first mechanical means, said monitor means, said detection means and said blood level detection means.

10. The apparatus of claim 8 wherein said monitor means is positioned proximate said second filter means.

11. The apparatus of claim 2 wherein said first filter means and said second filter means are integrally joined and positioned within said filter casing means.

12. The apparatus of claim 11 further comprising mechanical means associated with said reinfusion means for urging said blood therethrough.

13. The apparatus of claim 12 wherein said structure means for providing reverse filtration includes fluid retainer means in fluid communication with said filtration chamber for supplying fluid to said filtration chamber, and clamp means associated with said fluid retainer means for selectively preventing said fluid from being supplied to said filtration chamber.

14. The apparatus of claim 13 wherein said fluid retainer means is said washing fluid retainer means, and wherein said apparatus further includes an afferent line connected to said washing fluid retainer means to provide fluid communication with said filtration chamber of said second filter means.

15. The apparatus of claim 13 further comprising mechanical means for urging fluid from said fluid retainer means.

16. The apparatus of claim 15 further including a filtrate conduit interconnected between said filtration chamber and said filtrate retainer means for conducting filtrate therebetween, and clamp means associated with said filtrate conduit for selectively preventing filtrate from flowing through said filtrate conduit.

17. The apparatus of claim 16 wherein said mechanical means is also associated with said filtrate conduit for urging filtrate along said filtrate conduit.

18. The apparatus of claim 1 further comprising vacuum regulation means associated with said vacuum source for regulating the amount of negative pressure provided by said vacuum source to said apparatus.

19. An apparatus for treating autologous blood taken from a patient for reinfusion to the patient comprising:
suction means for aspirating blood from a wound site;
first conduit means for conducting said aspirated blood from said suction means;
washing fluid retainer means for retaining washing fluid for admixing with said aspirated blood;
second conduit means interconnected between said washing fluid retainer means and said first conduit for conducting washing fluid therebetween;
first filter means for removing emboli and large particulates from said aspirated blood, said first filter means being connected to said first conduit means;
filter casing means for enclosing said first filter means therein;
vacuum connector means associated with said first filter means for attaching a source of vacuum thereto;
reservoir means associated with said filter casing means for collecting filtered blood from said first filter means;
second filter means for filtering excess fluids and particulates from said blood;
third conduit means interconnected between said reservoir means and said second filter means for conducting blood therebetween;
fourth conduit means interconnected between said second filter and said reservoir for conducting filtered blood therebetween;
filtrate container means in fluid communication with said second filter means for containing said excess fluids and particulates filtered from said blood by said second filter means;
structure means connectable to said second filter means for providing movement of fluid through said second filter means to effect reverse filtration relative to said second filter means;
fifth conduit means interconnected between said second filter means and said filtrate container means for conducting filtrate therethrough; and
reinfusion means associated with said blood collection means for reinfusing purified blood to the patient.

20. The apparatus of claim 19 wherein said washing fluid retainer means is positioned below said relative height of said suction means.

21. The apparatus of claim 20 wherein said second filter includes a circulation chamber and a filtration chamber, said circulation chamber being in fluid communication with said first filter means, and said filtration chamber being in fluid communication with said structure means for providing reverse filtration.

22. The apparatus of claim 21 wherein said structure means for providing reverse filtration includes fluid retainer means in fluid communication with said filtration chamber for supplying fluid to said filtration chamber, and clamp means associated with said fluid retainer means for selectively preventing said fluid from being supplied to said filtration chamber.

23. The apparatus of claim 22 further comprising detection means associated with said filter casing means for detecting blood levels therein and monitor means associated with said reinfusion means for monitoring blood cellular component levels.

24. A method of obtaining and treating autologous blood for reinfusion into a patient comprising: providing apparatus for treating autologous blood comprising:
aspiration means for aspirating blood from a patient;

a source of washing fluid, first filter means for removing emboli and particulates from said blood;

a source of vacuum associated with said first filter means;

second filter means for removing excess fluid and particulates from said blood;

structure means for providing movement of fluid through said second filter to effect reverse filtration therethrough;

monitoring means for evaluating blood component levels; and reinfusion means;

aspirating blood from said patient using said aspiration means;

admixing said blood with washing fluid from said source of washing fluid;

filtering said admixture of blood and washing fluid through said first filter means to remove emboli and particulates;

filtering said admixture through said second filter means to remove particulates and excess fluid;

selectively providing fluid to said second filter means from said structure means for providing reverse filtration to effect intermittent reverse filtration;

monitoring said filtered blood cellular volume fraction in said blood; and reinfusing said filtered blood into said patient.

25. The method according to claim 24 further comprising filtering said blood after monitoring said filtered blood and prior to reinfusing said filtered blood into said patient.

* * * * *

UNITED STATES PATENT AND TRADEMARK OFFICE
CERTIFICATE OF CORRECTION

PATENT NO. : 5,215,519

DATED : 6/1/93

INVENTOR(S) : U. Ramakrishna Shettigar

It is certified that error appears in the above-indentified patent and that said Letters Patent is hereby corrected as shown below:

In Column 2, line 2, change "technique" to --techniques--;

In Column 2, line 49, after "unit" change the semicolon to a colon;

In Column 3, line 40, after "Compact" insert quotation marks;

In Column 8, line 62, change "22" to --46--;

In Column 10, line 47, after "patient" insert a period;

In Column 10, line 56, after "52" insert a period;

In Column 10, line 68, change "60" to --68--;

In Column 11, line 11, change "60" to --68--;

In Column 11, line 27, change "60" to --52--;

In Column 13, line 31, change "clamp" to --valve--;

In Column 13, line 35, change "clamp" to --valve--;

In Column 13, line 36, change "clamp" to --valve--;

In Column 13, line 47, change "clamp" to --valve--;

In Column 13, line 48, change "clamp" to --valve--;

In Column 14, line 51, insert a comma after "such";

In Column 15, line 50, change "filter 90" to --filter 88--;

UNITED STATES PATENT AND TRADEMARK OFFICE
CERTIFICATE OF CORRECTION

PATENT NO. : 5,215,519
DATED : June 1, 1993
INVENTOR(S) : U. Ramakrishna Shettigar It is certified that error appears in the above-indentified patent and that said Letters Patent is hereby corrected as shown below:

Drawings: delete Figs. 6-13.

Signed and Sealed this

Twenty-second Day of February, 1994

Attest:

BRUCE LEHMAN

Attesting Officer     Commissioner of Patents and Trademarks